(12) United States Patent
Lin (10) Patent No.: US 9,839,666 B2
(45) Date of Patent: Dec. 12, 2017

(54) PEPTIDE AND A USE THEREOF (71) Applicant: WELL RESOURCES LIMITED, Hong Kong (CN)

(72) Inventor: Chenlung Lin, Kaohsiung (CN)

(73) Assignee: Wells Resources Limited, Hong Kong (HK)

( * ) Notice: Subject to any disclaimer, the term of this patent is extended or adjusted under 35 U.S.C. 154(b) by 0 days.

(21) Appl. No.: 15/210,323

(22) Filed: Jul. 14, 2016

(65) Prior Publication Data

US 2016/0375092 A1 Dec. 29, 2016

Related U.S. Application Data (62) Division of application No. 14/394,927, filed as application No. PCT/CN2012/000725 on May 25, 2012, now Pat. No. 9,422,336.

(51) Int. Cl.
*A61K 38/10* (2006.01)
*C07K 7/08* (2006.01)
*C07K 14/81* (2006.01)

(52) U.S. Cl.
CPC ............... *A61K 38/10* (2013.01); *C07K 7/08* (2013.01); *C07K 14/8125* (2013.01)

(58) Field of Classification Search
CPC ..... A61K 38/10; C07K 14/81215; C07K 7/08
USPC .......................................................... 514/3.7
See application file for complete search history.

(56) References Cited

U.S. PATENT DOCUMENTS

| | | | |
|---|---|---|---|
| 2004/0115695 A1 | 6/2004 | Grasso | |
| 2008/0261869 A1 | 10/2008 | Shapiro | |
| 2010/0119588 A1 | 5/2010 | Sato et al. | |
| 2011/0003009 A1 | 1/2011 | Cheung | |

FOREIGN PATENT DOCUMENTS

| | | |
|---|---|---|
| CN | 101400790 A | 1/2009 |
| CN | 101848927 A | 9/2010 |
| JP | S53101515 A | 9/1978 |
| WO | 2005/019434 A2 | 3/2005 |
| WO | 2007/105565 | 9/2007 |
| WO | 2008/131508 | 11/2008 |
| WO | 2010/029537 A1 | 3/2010 |

OTHER PUBLICATIONS

Alpha-1-antiproteinase—rabbit (fragment), downloaded from https://www.ncbi.nlm.nih.gov/protein/109155?report=genbank&log$=protalign&blast_rank=1&RID=2UPpFTFT014, from Saito, A. et al.,"Differential interactions of rabbit plasma alpha-1-antiproteinases S and F with porcine trypsin," J. Biochem, 1988, 103, 247-253; 1 page.

"Designing Custom Peptides," from SIGMA Genosys, pp. 1-2. Accessed Dec. 16, 2004.
Berendsen JJC, "A Glimpse of the Holy Grail?" Science, 1998, 282:642-643.
Bonica JJ. The need of a taxonomy, Pain, 1979; 6(3), 247-8.
Bradley CM, Barrick D, "Limits of Cooperativity in a Structurally Modular Protein; Response of the Notch Ankyrin Domain to Analogous Alanine Substitutions in Each Repeat," J. Mol. Biol. 2002, 324: 373-386.
Breivik H. et al., Assessment of pain, Br J Anaesth, 2008, 101(1), 17-24.
Centers for Disease Control and Prevention. Influenza Viruses [Internet]. 2005. Available from: http://www.cdc.gov/flu/about/viruses/.
Centers for Disease Control and Prevention. Key Facts About Avian Influenza and Highly Pathogenic Avian Influenza A (H5N1) Virus. 2010. Available from: http://www.cdc.gov/flu/avian/gen-info/facts.htm.
Chaplan, SR et al. Quantitative assessment of tactile allodynia in the rat paw. J Neurosci Methods. 1994, 53(1), 55-63.
European Search report, issued for European Patent Application No. 12877443.7, dated Nov. 2, 2015.
Hoogerwerf WA, Shenoy M., Winstone, HH, Xiao S-y, He Z, Pasricha PJ, "Trypsin Mediates Nociception Via the Proteinase-Activated Receptor 2; A Poentially Novel Role in Pancreatic Pain," Gastroenterology, 2004, 127(3):883-891.
Imai, Y., et al. Inhibition of the release of bradykinin-like substances into the perfusate of rat hind paw by neurotropin. Jpn J Pharmacol, 1984; 36(1), 104-106.
International Search Report dated Mar. 7, 2013.
Klenk, H-D., et al. Avian Influenza: Molecular Mechanisms of Pathogenesis and Host Range. In: Mettenleiter TC, Sobrino F, editors. Animal Viruses: Molecular Biology. Norfolk: Caister Academic; 2008. p. 253-303.
Lackenby, A., et al.. The potential impact of neuraminidase inhibitor resistant influenza. Curr Opin Infect Dis., 2008, 21(6), 626-38.
Lynch JP, et al. Influenza: evolving strategies in treatment and prevention, Semin Respir Crit Care Med., 2007, 28(2), 144-58.
Main, CJ, et al. The Nature of Disability. In: Spanswick CC, Main CJ, editors. Pain management: an interdisciplinary approach. Edinburgh: Churchill Livingstone; 2000. p. 89-106.
Malmberg, AB et al., Partial sciatic nerve injury in the mouse as a model of neuropathic pain: behavioral and neuroanatomical correlates, Pain, 1998, 76, 215-222.
Matrosovich, MN, et al. Receptor Specificity, Host-range, and Pathogenicity of Influenza Viruses. In: Kawaoka Y, editor. Influenza Virology: Current Topics, 2006, p. 95-137.
Montalto, NJ, et al. Updated treatment for influenza A and B. Am Fain Physician. 2000, 62(11), 2467-76.
NCBI accession No. A41437, Jun. 18, 1933(Jun. 18, 1933).
NCBI accession No. NP_001164552, Jan. 13, 2010(Jan. 13, 2010).
Ngo JT, Marks J, Karplus M., "Computational Complexity, Protein Strucutre Prediction, and the Levinthal paradox," The Protein Folding Problem and Tertiary Structure Prediction, K. mere Jr. and S. Le Grand Edition, 1994, pp. 491-495.
Ono, T., et al. Clinical evaluation of Neurotropin tablets for low back pain—a double-blind comparative study. Japanese Pharmacol. 1981, 9(5), 299-307.

(Continued)

Primary Examiner — Julie Ha
(74) Attorney, Agent, or Firm — Barnes & Thornburg LLP (57) ABSTRACT

A peptide (SEQ ID NO:5), the use of the peptide for the inhibition of the activity of influenza virus and a pharmaceutical composition containing the peptide are described.

13 Claims, 5 Drawing Sheets

(56) References Cited

OTHER PUBLICATIONS

Raj, PP. Taxonomy and classification of pain. In: Kreider S, Beltrutti D, Lamberto A, Niv D, editors. The Handbook of Chronic Pain. New York: Nova Biomedical Books, 2007, 41-56.
Reed, LJ, et al., A Simple method for estimating fifty percent endpoints, American Journal of Hygiene, 1938, 27, 493-497.
Rowbotham, MC. Managing post-herpetic neuralgia with opioids and local anesthetics, Ann Neurol. 1994; 35 Suppl:S46-9.
Rudinger, J. "Characteristics of the amino acids as components of a peptide hormone sequence," Peptide Hormones, JA Parsons Edition, University Park Press, Jun. 1976, pp. 1-7.
Saito A, Sinohara H., "Differential Interactions of Rabbit Plasma alpha-1-Antiproteinases S and F with Porcine Trypsin," J. Biochem. 1988 103:247-253.
Saito et al., "Various forms of rabbit plasma alpha-1-antiproteinase." Biochem Mol Biol Int, (1998): 27-34.
Saito, A. et al., Cloning and Sequencing of cDNA Coding for Rabbit α-1-Antiproteinase F: Amino Acid Sequence Comparison of α-1-Antiproteinase of Six Mammals, Journal of Biochemistry, 1991, 109(1), 158-162.
Saito, A. et al., Differential Interactions of Rabbit Plasma α-1-Antiproteinases S and F with Porcine Trypsin, Journal of Biochemistry, 1988, 103 (2), 247-253.
Schinzel R., Drueckes P., "The phosphate recognition site of *Escherichia coli* maltodextrin phosphorylase," FEBS, Jul. 1991 286(1,2): 125-128.
Skevington, S. Biological Mechanisms of Pain. Psychology of pain, Chichester: Wiley; 1995, 8-23.
Soundararajan V., et al., Extrapolating from sequence—the 2009 H1N1 "swine" influenza virus. Nat Biotechnol, 2009, 27(6), 510-3.
Thienhaus, O., et al. The Classification of Pain. In: Weiner RS, editor. Pain Management: a Practical Guide for Clinicians. Boca Raton: CRC Press; 2002, 27-36.
Turk, DC, et al., Pain Terms and Taxonomies of Pain. In: Fishman SM, Ballantyne JC, Rathmell JP, editors. Bonica's Management of pain. 4th ed. Philadelphia, PA: Lippincott Williams & Wilkins, 2010, 17-25.
Voet, Donald and Judith, Second Edition, John Wiley Sons, Inc., 1995, pp. 235-241.
Wang, A., et al. Site-specific mutagenesis of the human interleukin-2 gene: structure-function analysis of the cysteine residues. Science, 1984, 224(4656), 1431-3.

SEQUENCE LISTING

```
<160> NUMBER OF SEQ ID NOS: 6

<210> SEQ ID NO 1
<211> LENGTH: 11
<212> TYPE: PRT
<213> ORGANISM: Oryctolagus cuniculus
<220> FEATURE:
<221> NAME/KEY: MISC_FEATURE
<222> LOCATION: (1)..(11)
<223> OTHER INFORMATION: residues 1-11 of rabbit alpha1-antiproteinase F

<400> SEQUENCE: 1

Asp Glu Ala Gln Glu Thr Ala Val Ser Ser His
1               5                   10

<210> SEQ ID NO 2
<211> LENGTH: 12
<212> TYPE: PRT
<213> ORGANISM: Oryctolagus cuniculus
<220> FEATURE:
<221> NAME/KEY: MISC_FEATURE
<222> LOCATION: (1)..(12)
<223> OTHER INFORMATION: residues 1-12 of rabbit alpha1-antiproteinase F

<400> SEQUENCE: 2

Asp Glu Ala Gln Glu Thr Ala Val Ser Ser His Glu
1               5                   10

<210> SEQ ID NO 3
<211> LENGTH: 13
<212> TYPE: PRT
<213> ORGANISM: Oryctolagus cuniculus
<220> FEATURE:
<221> NAME/KEY: MISC_FEATURE
<222> LOCATION: (1)..(13)
<223> OTHER INFORMATION: residues 1-13 of rabbit alpha1-antiproteinase F

<400> SEQUENCE: 3

Asp Glu Ala Gln Glu Thr Ala Val Ser Ser His Glu Gln
1               5                   10

<210> SEQ ID NO 4
<211> LENGTH: 13
<212> TYPE: PRT
<213> ORGANISM: Oryctolagus cuniculus
<220> FEATURE:
<221> NAME/KEY: MISC_FEATURE
<222> LOCATION: (1)..(13)
<223> OTHER INFORMATION: residues 2-14 of rabbit alpha1-antiproteinase F

<400> SEQUENCE: 4

Glu Ala Gln Glu Thr Ala Val Ser Ser His Glu Gln Asp
1               5                   10

<210> SEQ ID NO 5
<211> LENGTH: 14
<212> TYPE: PRT
<213> ORGANISM: Oryctolagus cuniculus
<220> FEATURE:
<221> NAME/KEY: MISC_FEATURE
<222> LOCATION: (1)..(14)
<223> OTHER INFORMATION: residues 1-14 of rabbit alpha1-antiproteinase F

<400> SEQUENCE: 5

Asp Glu Ala Gln Glu Thr Ala Val Ser Ser His Glu Gln Asp
1               5                   10
```

```
<210> SEQ ID NO 6
<211> LENGTH: 12
<212> TYPE: PRT
<213> ORGANISM: Oryctolagus cuniculus
<220> FEATURE:
<221> NAME/KEY: MISC_FEATURE
<222> LOCATION: (1)..(12)
<223> OTHER INFORMATION: residues 3-14 of rabbit alpha1-antiproteinase F

<400> SEQUENCE: 6

Ala Gln Glu Thr Ala Val Ser Ser His Glu Gln Asp
1               5                   10
```

PEPTIDE AND A USE THEREOF

CROSS-REFERENCE TO RELATED APPLICATIONS

This application is a divisional application of U.S. application Ser. No. 14/394,927, which is a U.S. national application under 35 USC §371(b) of PCT International Application No. PCT/CN2012/000725, filed May 25, 2012, the entire disclosures of all of which are incorporated herein by reference.

FIELD OF THE INVENTION

This disclosure relates to protein identification and pharmaceuticals fields. In particular, it relates to a natural peptide having potent analgesic effects and anti-influenza virus effect, its encoding polynucleotide, the preparation and uses thereof and a pharmaceutical composition containing said peptide.

BACKGROUND OF THE INVENTION

Pain is an unpleasant feeling often caused by intense or damaging stimuli. The International Association for the Study of Pain's widely defined 'pain' as "an unpleasant sensory and emotional experience associated with actual or potential tissue damage, or described in terms of such damage" (*Pain* 1979; 6:247-8). Pain is the most common reason for physician consultation in the United States (Raj P P. Taxonomy and classification of pain. In: Niv D, Kreitler S, Diego B, Lamberto A. The Handbook of Chronic Pain. Nova Biomedical Books 2007). It is a major symptom in many medical conditions, and can significantly interfere with a person's quality of life and general functioning (Breivik H, Borchgrevink P C, Allen S M, Rosseland L A, Romundstad L, Hals E K, Kvarstein G, Stubhaug A. Assessment of pain. Br J Anaesth. 2008; 101(1):17-24). In most cases, pain is usually transitory, lasting only until the noxious stimulus is removed or the underlying damage or pathology has healed. However, some painful conditions, such as rheumatoid arthritis, peripheral neuropathy, cancer and idiopathic pain, may persist for years. Pain that lasts a long time is called 'chronic', and pain that resolves quickly is called 'acute'. Traditionally, the distinction between acute and chronic pain has relied upon an arbitrary interval of time from onset; the two most commonly used markers are 3 months and 6 months since the onset of pain (Turk D C, Okifuji A. Pain terms and taxonomies of pain. In: Bonica J J, Loeser J D, Chapman C R, Turk D C, Butler S H. Bonica's management of pain. Hagerstwon, Md.: Lippincott Williams & Wilkins; 2001), though some researchers have placed the transition from acute to chronic pain at 12 months (Spanswick C C, Main C J. Pain management: an interdisciplinary approach. Edinburgh: Churchill Livingstone 2000). Others apply 'acute' to pain that lasts less than 30 days, 'chronic' to pain of more than six months, and 'subacute' to pain that lasts from one to six months (Thienhaus O, Cole B E. Classification of pain. In: Weiner R. Pain management: a practical guide for clinicians. Boca Raton: CRC Press; 2002).

In humans, the detection of peripheral pain begins at free nerve endings. The polymodal pain receptors and high threshold mechanoreceptors detect noxious stimuli such as strong mechanical forces, $H^+$, $K^+$, chemicals, and temperature. After detection of the stimuli, the sensation of pain travels from the periphery to the spinal cord (i.e., the spinothalamic tract), then decussate and cross via the anterior white commissure (in the spinal cord) before ascending contralaterally. Before reaching the brain, the spinothalamic tract splits into the lateral neo-spinothalamic tract and the medial paleo-spinothalamic tract (Skevington, S. M. Psychology of pain. Chichester, UK: Wile 1995; p 18), subsequently terminating at the ventral posterolateral nucleus of the thalamus, where they synapse on dendrites of the somatosensory cortex. Apart from noxious stimuli causing pain, injuries to a peripheral nerve in humans often results in a persistent neuropathic pain condition that is characterized by spontaneous, usually burning pain, allodynia (pain responses to non-noxious stimuli) and hyperalgesia (exaggerated pain responses to noxious stimuli). Although sympatholytic therapy is sometimes effective for relief of the pain, indicating that neuropathic pain is at least partly maintained by activity in the sympathetic nervous system, many patients do not respond. The effectiveness of opioids for neuropathic pain is also limited (Rowbotham M C. Ann Neurol 1994; 35:S46-S49), and somewhat controversial.

Acute pain is usually managed with medications such as analgesics and anesthetics. Management of chronic pain or neuropathic pain, however, is much more difficult. Many drugs help relieving acute pain, and in general they can be divided into non-opiod and opiod drugs. The non-opiod drugs include non-steroid anti-inflammatory drugs (NSAIDs), such as acetylsalicylic acid (aspirin) and COX-2 (cyclooxygenase-2) inhibitors. The term "nonsteroidal" in NSAIDs is used to distinguish these drugs from steroids, which, among a broad range of other effects, have a similar eicosanoid-depressing, anti-inflammatory action. As analgesics, NSAIDs are unusual in that they are non-narcotic. NSAIDs are usually indicated for the treatment of acute or chronic conditions where pain and inflammation are present.

Aspirin is often used as an analgesic to relieve minor aches and pains, as an antipyretic to reduce fever, or as an anti-inflammatory medication. Aspirin works well for dull, throbbing pain, but it is ineffective for pain caused by most muscle cramps, bloating, visceral distension, and acute skin irritation. As a post-surgery painkiller, aspirin is inferior to one of the NSAIDs ibuprofen and has a higher gastrointestinal toxicity. Furthermore, aspirin also has many contraindications and undesirable effects; for example, the use of aspirin needs to be cautious in people with peptic ulcers, mild diabetes, or gastritis. Even if none of these conditions is present, there is still an increased risk of stomach bleeding. The other category of NSAIDs is COX-2 selective inhibitor that directly targets COX-2, an enzyme responsible for inflammation and pain. Targeting selectivity for COX-2 reduces the risk of peptic ulceration, and is the main feature of celecoxib, rofecoxib and other members of this drug category. COX-2 inhibitors also have adverse effects, most notably an increased risk of renal failure, and some results have shown an increase in the risk for heart attack, thrombosis and stroke by a relative increase in thromboxane. Of note, Rofecoxib (commonly known as Vioxx) was taken off the market in 2004 because of these concerns.

An alternative category of analgesics is opioid drugs. An opioid is a psychoactive chemical that works by binding to opioid receptors, which are found principally in the central and peripheral nervous system and the gastrointestinal tract. The receptors in these organ systems mediate both the beneficial effects and the side effects of opioids. The analgesic effects of opioids are due to decreased perception of pain, decreased reaction to pain as well as increased pain tolerance. Opioids have long been used to treat acute pain (such as post-operative pain), and are invaluable in palliative care to alleviate the severe, chronic, disabling pain of terminal conditions such as cancer, and degenerative conditions such as rheumatoid arthritis. However, opioids should be used very cautiously in chronic non-cancer pain. High doses are not necessarily required to control the pain of advanced or end-stage disease. Tolerance (a physical reaction making the body less responsive to analgesic and other effects) is very likely to occur, making the opioid as the last option for pain control.

From the discussion above, it is clear that there is an urgent need to develop a new class of effective non-tolerant and non-sedative analgesics for controlling both severe acute pain and chronic pain.

A mixture of bioactive agents extracted from skin tissue of rabbits with inflammation elicited by inoculation of the virus Vaccinia variolae, which contain inhibitors against the kallikrein-kinin system, has been used for treatment of pain for decades (K. Ono, A. Inoue, and M. Nakamuro. Jpn Pharmacol Ther, 1981; 9:299-307). Pharmacological and clinical experiments showed that such a mixture of bioactive agents prepared from the rabbit skin have analgesic effects against all kinds of symptomatic neuralgia, lumbago, cholecystagia, angina, arterial embolism pains, acute pains from wound, burn and scald, pains in surgery or post-surgery, peptic ulcer pain, dysmenorrhea, labor pains posterior to childbirth, headache, pains induced by various tumor and so on. Studies also showed that the this mixture of bioactive agents can effectively promote activation of macrophage, significantly inhibit the activity of anti-complement in type II allergic reaction. The effects have linear correlation with the doses. So the drugs have effects on inhibiting inflammatory reaction correlated with immunity and improving immunity function. Furthermore, after a continuous 28-day intraperitoneally administration of the drugs prepared from the rabbit skin in rats, no rats died and no changes induced by the drugs existed in examinations of urine, eye, blood biochemistry, pathology and anatomy. Therefore, such analgesic drugs have little toxic effects (See US Patent application number: 20110003009). However, although peptide research on drug design and drug discovery is one of the most promising fields in the development of the new drug, there was no report that the researchers in this field focus on searching the active protein ingredients in the mixture, even though such a mixture has been in the market for several decades and with good effects for analgesia. Therefore, identification of the active ingredient(s) will help understanding the acting mechanism(s), and purification of the exact components responsible for analgesic effects will facilitate the preparation of well-delineated drug(s) for clinical use.

Influenzavirus A is a genus of the Orthomyxoviridae family of viruses. Strains of all subtypes of influenza A virus have been isolated from wild birds, although disease is uncommon. Some isolates of influenza A virus cause severe disease both in domestic poultry and, rarely, in humans ("Avian influenza ("bird flu")—Fact sheet". WHO.) Occasionally, viruses are transmitted from wild aquatic birds to domestic poultry, and this may cause an outbreak or give rise to human influenza pandemics (Klenk, et al. (2008). "Avian Influenza: Molecular Mechanisms of Pathogenesis and Host Range". Animal Viruses: Molecular Biology. Caister Academic Press & Kawaoka Y, ed. (2006). Influenza Virology: Current Topics. Caister Academic Press). Influenza A viruses are negative sense, single-stranded, segmented RNA viruses. There are several subtypes, labeled according to an H number (for the type of hemagglutinin) and an N number (for the type of neuraminidase). There are at least 16 different H antigens (H1 to H16) and nine different N antigens (N1 to N9). Different influenza viruses encode for different hemagglutinin and neuraminidase proteins; for example, the H5N1 virus designates an influenza A subtype that has a type 5 hemagglutinin (H) protein and a type 1 neuraminidase (N) protein. Furthermore, each virus subtype has mutated into a variety of strains with differing pathogenic profiles; some are pathogenic to one species but not others, and some are pathogenic to multiple species. Theoretically, 144 different combinations of these proteins are possible ("Influenza Viruses". Centers for Disease Control and Prevention. Nov. 18, 2005). Some variants are identified and named according to the isolate they resemble, thus are presumed to share lineage (example: Fujian flu virus-like), according to their typical host (example: human flu virus), according to their subtype (example: H3N2), and according to their deadliness (example: LP, low pathogenic). So a flu from a virus similar to the isolate A/Fujian/411/2002(H3N2) is called Fujian flu, human flu, or H3N2 flu.

"Human influenza virus" usually refers to those subtypes that spread widely among humans. Amongst all strains, H1N1, H1N2, and H3N2 are the only known influenza A virus subtypes currently circulating among humans (CDC, USA: Key Facts About Avian Influenza (Bird Flu) and Avian Influenza A (H5N1) Virus). Treatments for influenza include a range of medications and therapies that are used in response to disease influenza. Treatments may either directly target the influenza virus itself; or instead they may just offer relief to symptoms of the disease, while the body's own immune system works to recover from infection (Montalto N J, Gum K D, Ashley J V (2000). "Updated treatment for influenza A and B". Am Fam Physician 62 (11): 2467-76). The two main classes of antiviral drugs used against influenza viruses are neuraminidase inhibitors, such as zanamivir and oseltamivir, or inhibitors of the viral M2 protein, such as amantadine and rimantadine. These drugs can reduce the severity of symptoms if taken soon after infection and can also be taken to decrease the risk of infection. However, viral strains have emerged with drug resistance to both classes of drug. Like the development of bacterial antibiotic resistance, this can result from over-use of these drugs. For example, a recent study emphasized the urgent need for augmentation of oseltamivir (Tamiflu) stockpiles with additional antiviral drugs including zanamivir (Relenza) based on an evaluation of the performance of these drugs in the scenario that the 2009 H1N1 'Swine Flu' neuraminidase (NA) were to acquire the tamiflu-resistance (His274Tyr) mutation which is currently widespread in seasonal H1N1 strains (Venkataramanan Soundararajan, Kannan Tharakaraman, Rahul Raman, S. Raguram, Zachary Shriver, V. Sasisekharan, Ram Sasisekharan (2009). "Extrapolating from sequence—the 2009 H1N1 'swine' influenza virus". Nature Biotechnology 27 (6): 510-3). Another example is in the case of the amantadines treatment, which may lead to the rapid production of resistant viruses, and over-use of these drugs has probably contributed to the spread of resistance (Lynch J P, Walsh E E (April 2007). "Influenza: evolving strategies in treatment and prevention". Semin Respir Crit Care Med 28 (2): 144-58.).

Meanwhile, however, a few strains resistant to neuraminidase inhibitors have emerged and circulated in the absence of much use of the drugs involved, and the frequency with which drug resistant strains appears shows little correlation with the level of use of these drugs (Lackenby A, Thompson C I, Democratis J (December 2008). "The potential impact of neuraminidase inhibitor resistant influenza". Curr. Opin. Infect. Dis. 21 (6): 626-38.). Laboratory studies have also shown that it is possible for the use of sub-optimal doses of these drugs as a prophylactic measure contributing to the development of drug resistance (Lackenby A, Thompson C I, Democratis J (December 2008). "The potential impact of neuraminidase inhibitor resistant influenza". Curr. Opin. Infect. Dis. 21 (6): 626-38). Search for a newer class of anti-influenza virus with potency and less side-effects has become a challenge to the bio-medical community.

SUMMARY OF THE INVENTION

One purpose of the disclosure is to provide an analgesic peptide with the amino acid sequence as shown in SEQ ID NO: 5, its variant and derivative. Surprisingly, this peptide also shows anti-influenza A virus activity.

Another purpose of the disclosure is to provide polynucleotides encoding the peptide, its variant and/or derivative.

Still another purpose of the disclosure is to provide the preparation and uses of the peptide, its variant and/or derivative.

In one aspect, the present disclosure provides an isolated peptide comprising the amino acid sequence as shown in SEQ ID NO: 5, its conserved variants, its active fragments, and its active derivatives. Preferably, said peptide has the amino acid sequence of DEAQETAVSSHEQD as shown in SEQ ID NO: 5.

In another aspect, the present disclosure provides an isolated peptide comprising an amino acid sequence sharing at least 50% homology, for example, at least 60% homology, at least 70% homology, at least 80% homology or at least 90% homology, to the amino acid sequence as shown in SEQ ID NO: 5 and possessing the analgesic and/or anti-influenza A virus activity.

In another aspect, the present disclosure provides an isolated peptide comprising an amino acid sequence having one to seven (for example, one, two, three, four, five, six or seven) conserved amino acid substitutions compared to the amino acid sequence as shown in SEQ ID NO: 5 and possessing the analgesic and/or anti-influenza A virus activity.

In another aspect, the peptide disclosed herein, its variant and/or derivative are obtained by chemical synthesis.

In another aspect, the present disclosure provides an isolated polynucleotide comprising a nucleotide sequence sharing at least 50% homology to a nucleotide sequence selected from the group consisting of:
(a) a nucleotide sequence encoding a peptide comprising the amino acid sequence as shown in SEQ ID NO: 5, its variant and/or derivative, and
(b) the polynucleotide complementary to nucleotide sequence of (a);
wherein said peptide, its variant and/or derivative possessing the analgesic and/or anti-influenza A virus activity.

In another aspect, the present disclosure provides an isolated polynucleotide which encodes a peptide comprising the amino acid sequence as shown in SEQ ID NO: 5.

In another aspect, the present disclosure provides a vector comprising the above polynucleotide, and a host cell transformed with the vector or polynucleotide.

In another aspect, the present disclosure provides a method for producing a peptide having the activity of the peptide as shown in SEQ ID NO: 5, which comprises:
(a) culturing the above transformed host cell under the expression conditions;
(b) isolating the peptide of the present invention from the culture.

In another aspect, the present disclosure provides compounds that stimulate, promote and antagonize the activity of peptide as shown in SEQ ID NO: 5.

In another aspect, the present disclosure provides a pharmaceutical composition comprising an efficient amount of the peptide herein, its variant and/or derivative, and a pharmaceutically acceptable carrier. This pharmaceutical composition can be used to treat or relief the diseases and/or symptoms associated with pain in a subject. The diseases and/or symptoms associated with pain herein include, but not limited to those selected from all kinds of symptomatic neuralgia, lumbago, -cholecystagia, angina, arterial embolism pains, acute pains from wound, burn and scald, pains in surgery or post-surgery, peptic ulcer pain, dysmenorrhea, labor pains posterior to childbirth, headache, pains induced by various tumor. This pharmaceutical composition can also be used to inhibit the activity of influenza A virus in a subject. The influenza A virus herein preferably is selected from H5N1 and H1N1.

In another aspect, the present disclosure provides a method for the treatment of the diseases and/or symptoms associated with pain in a subject, the method comprising the administration to the subject of an effective amount of a peptide herein, its variant and/or derivative.

In another aspect, the present disclosure provides a method for the inhibition of the activity of influenza A virus in a subject, wherein the method comprising the administration to the subject of an effective amount of a peptide herein, its variant and/or derivative.

In another aspect, the present disclosure provides the use of a peptide herein, its variant and/or derivative in the preparation of a medicament for the treatment or remission of the diseases and/or symptoms associated with pain in a subject.

In another aspect, the present disclosure provides the use of a peptide herein, its variant and/or derivative in the preparation of a medicament for the inhibition of the activity of influenza A virus in a subject.

The other aspects of invention will be apparent to artisan in light of the teaching of the disclosure.

All publications mentioned in this specification are herein incorporated by reference to the same extent as if each individual publication was specifically and individually indicated to be incorporated by reference in its entirety unless otherwise specifically noted.

BRIEF DESCRIPTION OF THE DRAWINGS

The following drawings illustrate the embodiments, and do not limit the scope of invention defined in the claims.

FIG. 7. Peptide 5 as shown in SEQ ID NO: 5 has potent effects in inhibiting the replication of H5N1 and H1N1 viruses in vitro. Peptide 5 as shown in SEQ ID NO: 5 was dissolved in pure water and was added (0, 0.001, 0.01, 0.1, 1 and 10 μM) into the monolayered MDCK cells that were simultaneously infected by various strains of H5N1 (left panel) or H1N1 viruses (right panel) at 5,000 pfu/ml. After 3 days, the plaque number was counted manually and was normalized against the untreated control (i.e., 0 μM).

Note:

For A/Vietnam/1194/04(H5N1):

(1) No statistical significance between no treatment and treatment with 0.1 μM
(2) p<0.01 between no treatment and treatment with 1 μM
(3) p<0.001 between no treatment and treatment with 10 μM Whereas for both A/Hong Kong/97(H5N1) and A/goose/Taichung/Q156/05(H5N1):

(1) p<0.05 between no treatment and treatment with 0.1 μM
(2) p<0.005 between no treatment and treatment with 1 μM
(3) p<0.001 between no treatment and treatment with 10 μM For pandemic H1N1/2009:

(1) no statistical significance between no treatment and 0.01 μM
(2) p<0.05 between no treatment and treatment with 0.1 μM
(3) p<0.005 between no treatment and treatment with 1 μM
(4) p<0.001 between no treatment and treatment with 10 μM For A/Taiwan/01/86(H1N1):

(1) p<0.05 between no treatment and treatment with 0.01 μM
(2) p<0.01 between no treatment and treatment with 0.1 μM
(3) p<0.005 between no treatment and treatment with 1 μM
(4) p<0.001 between no treatment and treatment with 10 μM.

DETAILED DESCRIPTION OF THE INVENTION

The embodiments of the peptides, pharmaceutical compositions, uses and methods of the present disclosure are intended to be illustrative and not limiting. Modifications and variations can be made by the skills in the art in light of the above teachings, specifically those that may pertain to alterations in the peptides maintaining near native functionally with respect to analgesic and/or anti-influenza A virus effect. Therefore, it should be understood that changes may be made in the particular embodiments disclosed which are within the scope of what is described.

As used herein, the peptide with the amino acid sequence as shown in SEQ ID NO: 5 is a fragment of rabbit α1-antiproteinase F.

As used herein, the term "isolated" refers to a substance which has been isolated from the original environment. For naturally occurring substance, the original environment is the natural environment. E.g., the polynucleotide and peptide in a naturally occurring state in the viable cells are not isolated or purified. However, if the same polynucleotide and peptide have been isolated from other components naturally accompanying them, they are isolated or purified.

The peptide of the disclosure may be a recombinant, natural, or synthetic peptide, preferably a recombinant peptide. The peptide of the disclosure may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the recombinant production, the peptide may be glycosylated or non-glycosylated.

As used herein, the terms "derivative" and "variant" mean the peptide that essentially retains the same biological functions or activity of natural peptide of DEAQETAVSSHEQD (SEQ ID NO: 5).

As used herein, the term "derivative" used herein includes, but is not limited to, (i) one in which one or more of the amino acid residues include a substituent group, (ii) one in which the peptide is fused with another compound, such as a compound to increase the half-life of the peptide (for example, polyethylene glycol), (iii) one in which the additional amino acids are fused to the peptide, such as a leader or secretary sequence or a sequence used for purifying peptide or proprotein, or (iv) one in which the peptide is modified by some modifications. Such derivatives are known to the artisans based on the teachings herein.

As used herein, the term "modifications" (which do not normally alter primary sequence) include in vivo or in vitro chemical derivation of peptides, e.g., acelylation, or carboxylation. Also included are modifications of glycosylation, e.g., those made by modifying the glycosylation patterns of a peptide during its synthesis and processing or in the further processing steps, e.g., by exposing the peptide to glycosylation enzymes (e.g., mammalian glycosylating or deglycosylating enzymes). Also included are sequences having phosphorylated amino acid residues, e.g., phosphotyrosine, phosphoserine, phosphothronine, as well as sequences modified to improve the resistance to proteolytic degradation or to optimize solubility properties.

As used herein, the term "variant" includes, but is not limited to, deletions, insertions and/or substitutions of several amino acids, preferably several conserved amino acid substitutions (typically 1-7, preferably 1-6, more preferably 1-5, even more preferably 1-4, still more preferably 1-3, most preferably 1-2), and addition of one or more amino acids (typically less than 20, preferably less than 10, more preferably less than 5) at C-terminal, N-terminal or inside the peptide. For example, the protein functions are usually unchanged when an amino residue is substituted by a similar or analogous one, e.g. substituted with a conserved or non-conserved amino acid residue (preferably a conserved amino acid residue). Further, the addition of one or several amino acids at C-terminal and/or N-terminal usually does not change the protein function.

As used herein, the term "conserved amino acid substitutions" means a peptide formed by substituting at most 7, preferably at most 6, more preferably 5, and most preferably at most 3 amino acids with the amino acids having substantially the same or similar property, as compared with the amino acid sequence of DEAQETAVSSHEQD (SEQ ID NO: 5). Preferably, these conserved mutants are formed by the substitution according to Table 1.

TABLE 1

| Initial residue | Representative substitution |
|---|---|
| Asp (D) | Glu |
| Glu (E) | Asp |
| Ala (A) | Val; Leu; Ile |
| Gln (Q) | Asn |
| Thr (T) | Ser |
| Val (V) | Ile; Leu; Met; Phe; Ala |
| Ser (S) | Thr |
| His (H) | Asn; Gln; Lys; Arg |

The polynucleotide of invention may be in the forms of DNA and RNA. DNA includes cDNA, genomic DNA, and synthetic DNA, etc., in single strand or double strand form. The polynucleotide of invention may be a degenerate sequence. As used herein, the term "degenerate sequence" means that there are different sequences which encode the same protein due to the degeneracy of codons.

The term "polynucleotide encoding the peptide" includes the polynucleotide encoding said peptide and the polynucleotide comprising additional and/or non-encoding sequence.

The polynucleotide encoding the peptide herein can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. Once the sequence is obtained, one can produce lots of the sequences by recombinant methods. Usually, said sequence is cloned into a vector which is then transformed into a host cell. The sequence is isolated from the amplified host cells using conventional techniques.

The invention further relates to a vector comprising the polynucleotide of the disclosure, a genetic engineered host cell transformed with the vector or the polynucleotide of the disclosure, and the method for producing the peptide by recombinant techniques.

The recombinant peptides can be expressed or produced by the conventional recombinant DNA technology (Science, 1984; 224:1431), using the polynucleotide sequence of invention. Generally, it comprises the following steps:
(1) transfecting or transforming the appropriate host cells with the polynucleotide encoding the peptide or the vector containing the polynucleotide;
(2) culturing the host cells in an appropriate medium;
(3) isolating or purifying the protein from the medium or cells.

In the invention, the polynucleotide sequences herein may be inserted into a recombinant expression vector. The term "expression vector" means a bacterial plasmid, bacteriophage, yeast plasmid, plant virus or mammalian cell virus, such as adenovirus, retrovirus or any other vehicles known in the art. Any plasmid or vector can be used to construct the recombinant expression vector as long as it can replicate and is stable in the host. One important feature of expression vector is that the expression vector typically contains a replication origin, a promoter, a marker gene as well as the translation regulatory components.

The known methods can be used to construct an expression vector containing the sequence herein and appropriate transcription/translation regulatory components. These methods include in vitro recombinant DNA technique, DNA synthesis technique, in vivo recombinant technique, etc. The DNA sequence is efficiently linked to the proper promoter in an expression vector to direct the synthesis of mRNA. The exemplary promoters are lac or trp promoter of *E. coli*; PL promoter of λ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

As used herein, the term "host cell" includes prokaryote, e.g., bacteria; primary eukaryote, e.g., yeast; advanced eukaryotic, e.g., mammalian cells. The representative examples are bacterial cells, e.g., *E. coli, Streptomyces, Salmonella typhimurium*; fungal cells, e.g., yeast; plant cells; insect cells e.g., *Drosophila* S2 or Sf9; animal cells e.g., CHO, COS or Bowes melanoma, etc.

As used herein, the term "analgesic effect" includes "anti-hyperalgesia effect" and "anti-allodynia effect". However, these three terms could be used separately because they indicate pain relief in different diseases or model.

As used herein, the term "the subject" includes human, non-human mammalians (for example, cow, sheep, rabbit, dog, mouse, rat, monkey, etc.) and domestic poultry.

The invention also provides a pharmaceutical composition comprising safe and effective amount of the peptide herein, its variant and/or derivative in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 ug-50 mg/kg body weight or more per day. Moreover, the peptide of invention can be administrated together with other therapeutic agents.

Previous experiment evidence shows that crude extract of the inflammatory rabbit skins induced by inoculation of Vaccinia virus can exert its pharmacological effect on analgesia. To identify the exact components for pain relief, as demonstrated by its parental agent AGC®, we employed a proteomic approach to determine the differences in the mass-to-charge ratios (m/z) by using nano LC-MS/MS. Through sophisticated chemical purification and database search, the inventors identified a peptide sequence of DEAQETAVSSHEQD (SEQ ID NO: 5) that possesses potent analgesic, anti-hyperalgesia, anti-allodynia and anti-influenza A virus effects.

The invention is further illustrated by the following examples. These examples are only intended to illustrate the invention, but not to limit the scope of the invention. For the experimental methods in the following examples, they were performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

Example 1: Peptide Identification

A. Samples Preparation

The mixture of the bioactive agents extracted from skin tissues of rabbits with inflammation elicited by inoculation of the virus Vaccinia variolae was prepared as described (Y. Imai, K. Saito, S. Maeda et al. Inhibition of the release of bradykinin-like substances into the perfusate of rat hind paw by neurotropin. Jpn J Pharmacol 1984, 36:104-106) and was provided by the Vanworld Pharmaceutical Co Ltd, Rugao, China, with a trade name of AGC® (10 U/mL, 25 mL/vial). Around 200 μL of the crude preparation of AGC® was dried in a vacuum centrifuge. The lyophilized material was reconstituted with 100 μL of 0.5 M ammonia bicarbonate buffer (pH 8.5) containing 8 M urea and 0.5 M dithiothreitol (DTT) for 1 hr at 37° C., and for another 2 hr at 4° C. under dark condition when 10 μL of 0.5 M iodoacetamide (IAM) was added for alkylation. Subsequently, the resulting solutions were then digested with 0.2 μg of trypsin for 18 h at 37° C., and then the trypsin-digested solutions were acidified by 10% trifluoroacetic acid (TFA)/$H_2O$ to pH 3.0 value. After the reaction, the totally acidified solutions were applied onto the reverse phase C18 column pre-equilibrated with 200 μL of 0.1% TFA/$H_2O$ (pH 3.0). The column was also washed with 200 μL of 0.1% TFA/$H_2O$ (pH 3.0) and then eluted with a stepwise acetonitrile gradient from 50% to 100% in 0.1% TFA at room temperature.

B. Nano-LC-MS/MS Analysis

The eluted fractions were collected, dried in a vacuum centrifuge, and then reconstituted in 10 μL of 0.1% formic acid (FA) in $H_2O$ and analyzed by LTQ Orbitrap XL (Thermo Fisher Scientific, San Jose, Calif.). Reverse phase nano-LC separation was performed on an Agilent 1200 series nanoflow system (Agilent Technologies, Santa Clara, Calif.). A total of 10 μL sample from fraction was loaded onto an Agilent Zorbax XDB C18 precolumn (0.35 mm, 5 μm), followed by separation using a C18 column (i.d. 75 μm×25-cm, 3 μm, Micro Tech, Fontana, Calif.). The mobile phases used were (A) 0.1% FA and (B) 0.1% FA in 100% ACN. A linear gradient from 5% to 35% (B) over a 90-min period at a flow rate of 300 nL/min was applied. The peptides were analyzed in the positive ion mode by applying a voltage of 1.8 Kv to the injection needle. The MS was operated in a data-dependent mode, in which one full scan with m/z 300-2000 in the Orbitrap (R=60 000 at m/z 400) using a rate of 30 ms/scan. The six most intense peaks for fragmentation with a normalized collision energy value of 35% in the LTQ were selected. A repeat duration of 30 s was applied to exclude the same m/z ions from the reselection for fragmentation. The reconstituted liquid as control, also treated by reduction, alkylation and desalting, was acidified and subject to nano-LC-MS/MS analysis as mentioned above, except for trypsin digestion.

C. Database Search and Identification

Peptides were identified by peak lists converted from the nanoLC-MS/MS spectra by searching against animal taxonomy in the NCBI databases for exact matches using the MASCOT search program (<http://www.matrixscience.com>; Hirosawa et al., 1993). The mass tolerance of both precursor ion and fragment ions was set to 0.8 Da. Searches were performed to allow for the fixed modification as carbamidomethylation (C), and no trypsin as an enzyme. The resultant identification had a statistically significant (P≤0.05) peptide score (based on combined MS and MS/MS spectra) and best ion score (based on MS/MS spectra).

D. Results

Figure 1:
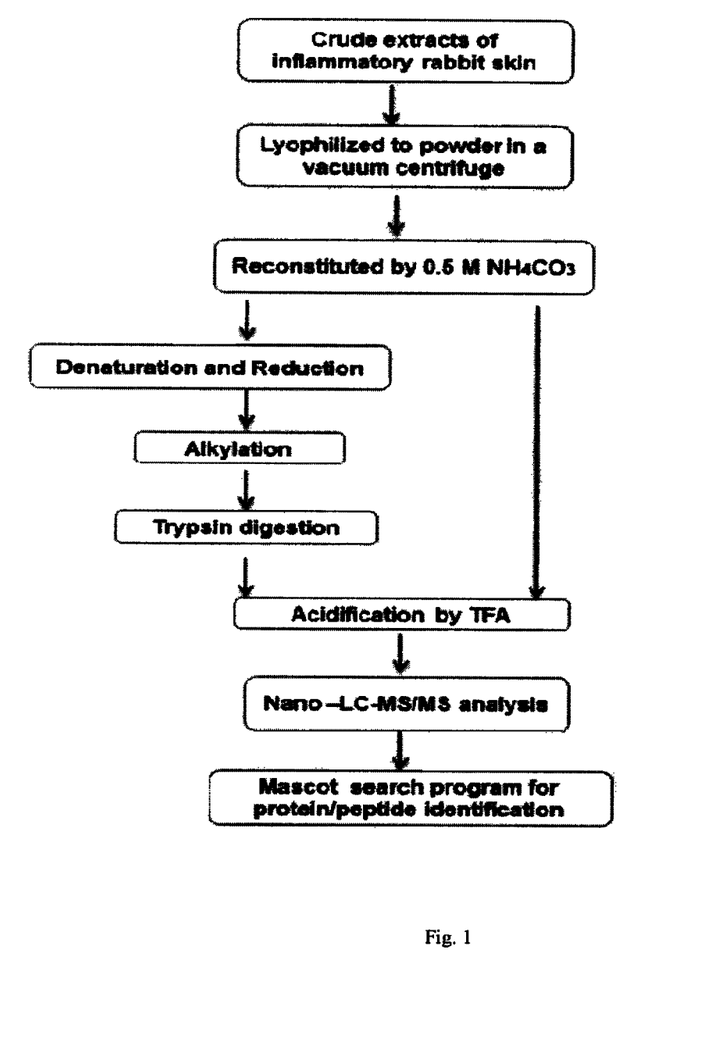
FIG. 1. Schematic representation of the procedures used for screening peptide/small peptide-level analgesic agents from crude extracts of the inflammatory rabbit skins induced by inoculation of Vaccinia virus.
Figure 2:
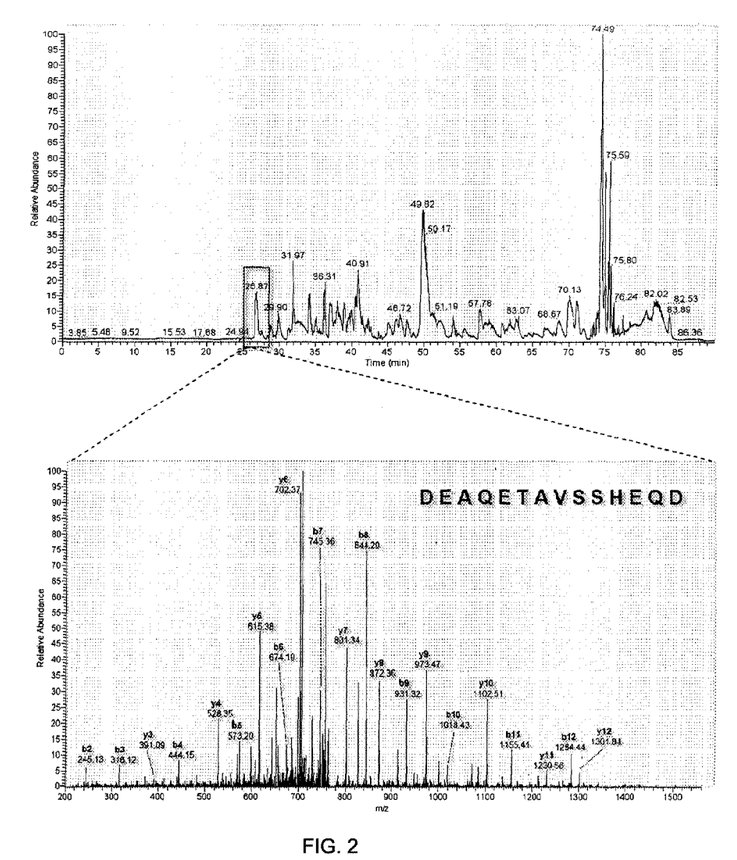
FIG. 2. Identification of functional peptide(s). The MS/MS spectrum of the doubly charged ion m/z 772.745 is shown. The amino acid sequence as shown in SEQ ID NO: 5 was determined from MS differences in the y- and b-fragment ions series and matched residues 1-14 of rabbit α1-antiproteinase.

The mass spectral patterns of protein fragments generated with or without trypsin digestion were then used for comparison with those of previously known proteins deposited in databanks to confirm peptide sequences, which can be used for identification of intact proteins (protein ID). Therefore, we can achieve an extensive coverage of peptides by shotgun analysis, elucidate the expression profiles of peptides or small peptides and identify sequences as well as the biochemical characterization. A flow chart of the methods used in this work and all the peptides identified with their biochemical characterization are listed in Table 2. The representative peptide peak from MS/MS analysis was detected (FIG. 2), resulting in confident protein identification by MASCOT searching. The MS/MS spectrum of the doubly charged ion m/z 772.745 is shown. The amino acid sequence DEAQETAVSSHEQD as shown in SEQ ID NO: 5, determined from MS differences in the y- and b-fragment ions series and matched with residues 1-14 of rabbit α1-antiproteinase F, which is different from that in human, mouse or in cattle. In addition, it also shares no homology with the other analgesia-related peptides including opioid agonist DAGO. According to computational prediction, it is linear and is unlikely to have structures like α-helix, β-sheet, β-turn, or bend region.

TABLE 2

Characterization of six small peptides identified by MS/MS spectra from nano LC-MS/MS analysis.

| Peptide sequence | PI/Mass (Da) |
|---|---|
| SEQ ID NO: 1: DEAQETAVSSH (Pepetide 1) | 4.13/1173.16 |
| SEQ ID NO: 2: DEAQETAVSSHE (Pepetide 2) | 4.00/1302.27 |
| SEQ ID NO: 3: DEAQETAVSSHEQ (Pepetide 3) | 4.00/1430.40 |
| SEQ ID NO: 4: EAQETAVSSHEQD (Pepetide 4) | 4.00/1430.40 |
| SEQ ID NO: 5: DEAQETAVSSHEQD (Pepetide 5) | 3.83/1545.49 |
| SEQ ID NO: 6: AQETAVSSHEQD (Pepetide 6) | 4.13/1304.29 |

Example 2: Analgesic Effects In Vivo

The peptides were synthesized at a commercial facility of Mission Biotech Co. (MB, Taipei, Taiwan) using the solid phase Fmoc chemistry and purified by reverse phase high-performance liquid chromatography to a purity of >90% and validated by MS. The final peptide products were dissolved in DMSO for experimental use.

For acute visceral pain model in mice, C57BL/6 male mice weighing 20-25 gm were intra-peritonealy injected with 1 mg morphine (as a positive control) or synthetic peptide 1-6 (SEQ ID NO:1-6, 2 mg each). Thirty minutes afterwards, mice were subsequently injected with 1 ml of 1% acetic acid intra-peritoneally. The onset of the $1^{st}$ writhing and the frequency of writhing in the following 30 minutes were recorded.

Figure 3:
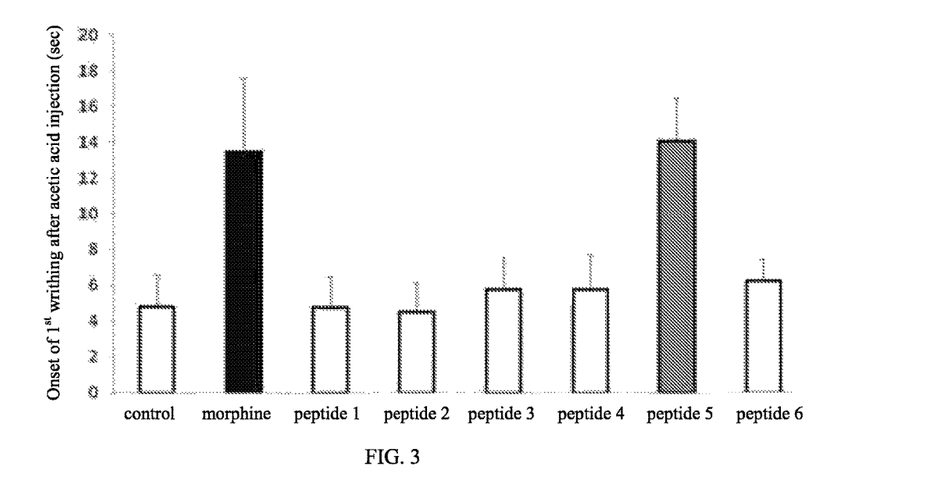
FIG. 3. The Peptide 5 (SEQ ID NO: 5) has the most superior pain-relieving effect to other peptides and is comparable to 1 mg morphine, as shown by a significant delay in the onset of the pain induced by intra-peritoneal injection of acetic acid (n=6). Note: p<0.005 between peptide 5 vs peptide 1, 2, 3, 4, or 6; p>0.05 between peptide 5 vs morphine; and control: water alone.
Figure 4:
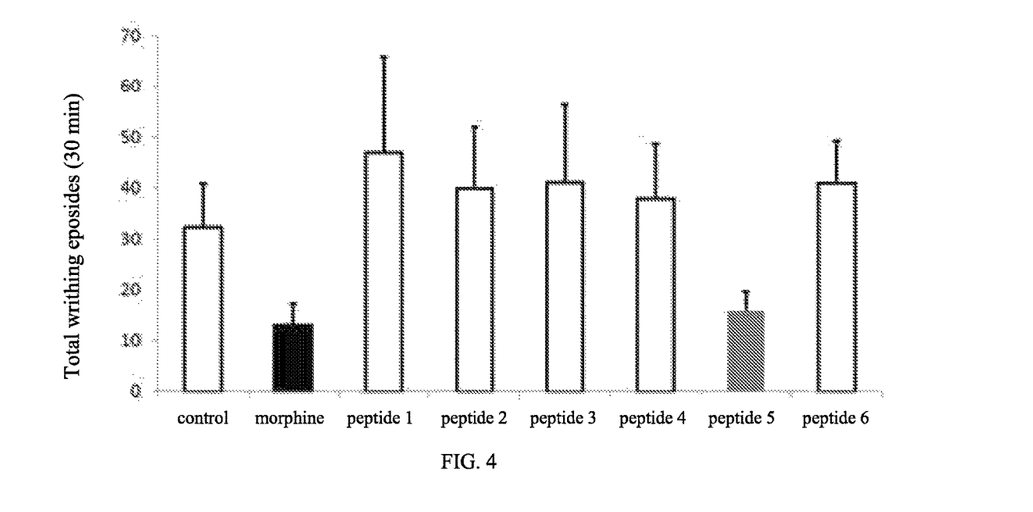
FIG. 4. Peptide 5 as shown in SEQ ID NO: 5 also caused significant reduction in the total writhing number in 30 minutes after acetic acid injection (n=6). Note: p<0.01 between peptide 5 vs peptide 1, 2, 3, 4, or 6; p>0.05 between peptide 5 vs morphine. Control: water alone.

The peptide 5 as shown in SEQ ID NO: 5 (a 14-amino acid peptide) has similar pain-relieving effects comparable to 1 mg morphine as shown in delayed latency of the paw withdrawal (FIG. 3) and reduced total writhing episodes measured in 30 min (FIG. 4).

Example 3: Anti-Hyperalgesia Effects

C57BL/6 male mice weighing 20-25 gm were used. Surgical procedures were performed under Halothane (2-3%) anesthesia. Partial sciatic nerve injury was made by tying a tight ligature with 9-0 silk suture around ⅓ to ½ the diameter of the sciatic nerve, as had been described (Malmberg A B and Basbaum A I. Pain 1998; 76:215-222). In mice with sham operation, the sciatic nerve was exposed but not ligated. The mice were subsequently habituated to the test environment for at least 1 hour before thermal test and von Foley hair test. In thermal test, the paw withdrawal latency was determined as an indicator for pain. In the von Foley test, the stimulus intensity was adjusted to give a 10-second withdrawal latency in the normal mouse, while the cutoff in the absence of a response was 20 seconds. The mechanical sensitivity with von Foley hairs was assessed by the up-down paradigm (Chaplan et al, J Neurosci Methods 1994; 53:53-66). The filament for the testing paradigm was chosen to be 0.3-gm.

Figure 5:
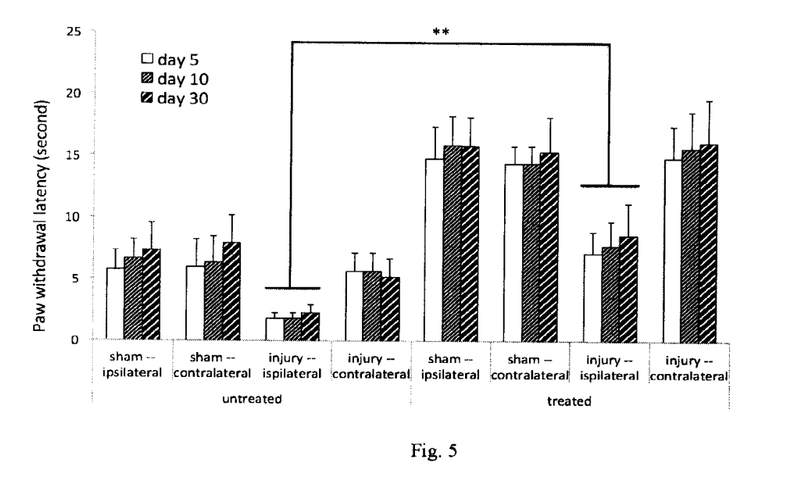
FIG. 5. Peptide 5 possessed potent analgesic effects of neurogenic origin. In thermal stimulation, treatment with intra-peritoneal injection of 2 mg peptide 5 as shown in SEQ ID NO: 5 (DEAQETAVSSHEQD) significantly reduced the temperature-induced pain of the sciatic nerve injured limb (hyperalgesia). Data are expressed as mean±SD in times (seconds). N=6. Note: **p<0.005 (by ANOVA) between untreated and treated injured ipsilateral limb on day 5, 10 or 30.

The peptide 5 as shown in SEQ ID NO: 5 was tested for its anti-hyperalgesia effects in mice receiving sciatic nerve ligation. Results from the thermal test of the sham operated mice and the nerve injured mice were compared in parallel on day 5, 10 and 30 after the surgery. Results clearly demonstrated that the limbs with nerve injury had hyperalgesia, as demonstrated by significantly reduced paw withdrawal latencies, compared to that of the contralateral limb or sham-operated limbs (FIG. 5). Furthermore, intra-peritoneal injection of 2 mg peptide 5 as shown in SEQ ID NO: 5 (labeled as "treated") indeed could significantly increase the tolerance to the heat-induced pain, as demonstrated by an increase of the paw withdrawal latency (FIG. 5), in comparison to control mice given DMSO solvent (labeled as "untreated").

Example 4: Anti-Allodynia Effects

Figure 6:
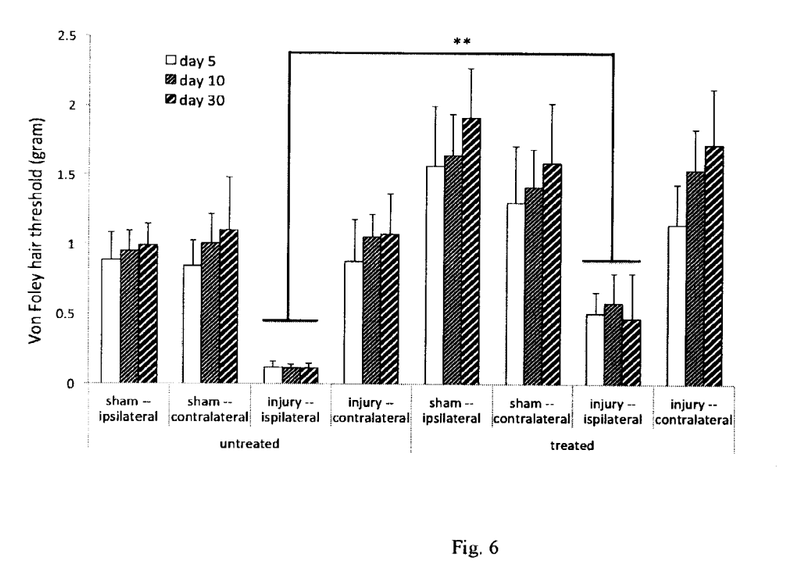
FIG. 6. Peptide 5 as shown in SEQ ID NO: 5 possessed potent effects over thermal allodynia of limbs with or without nerve injury. In mechanical stimulation, treatment with intra-peritoneal injection of 2 mg peptide 5 as shown in SEQ ID NO: 5 significantly reduced the thermal allodynia of the sciatic nerve injured limb. Data are expressed as mean☐SD in von Foley hair threshold (in grams). N=6 per time point. Note: **p<0.005 (by ANOVA) between untreated and treated injury-ipsilateral limb on day 5, 10 or 30.

The same animal model in example 3 was used. The peptide 5 as shown in SEQ ID NO: 5 was tested for its anti-allodynia effects in mice receiving sciatic nerve ligation. Results from the mechanical stimulation (von Foley test) of the sham operated mice and the nerve injured mice were compared in parallel on day 5, 10 and 30 after the surgery. Results clearly demonstrated that the limbs with nerve injury had hyper-allodynia, as demonstrated by significantly lower von Foley threshold, compared to that of the contralateral limb or sham-operated limbs (FIG. 6). Furthermore, intra-peritoneal injection of 2 mg peptide 5 as shown in SEQ ID NO: 5 (labeled as "treated") indeed could significantly increase the tolerance to mechanical stimuli, as demonstrated by an increase of the von Foley threshold (FIG. 6), in comparison to control mice given pure water (labeled as "untreated").

Example 5: Anti-Virus Effects

A. Viruses and Cells

The H5N1 isolates A/Vietnam/1194/04 and A/Hong Kong/97 were obtained from the Department of Microbiology, the University of Hong Kong. The virus was used of $3\times10^5$ $TCID_{50}$ for experiments. A/Taiwan/01/86 (H1N1) was also used at $3\times10^5$ $TCID_{50}$ for experiments. The H5N1 experiments were conducted in a biosafety level (BSL) 3+ containment facility. Aliquots of stock viruses were stored at $-80°$ C. Madin-Darby canine kidney (MDCK) cells were obtained from the American Type Culture Collection (Manassas, Va., USA) and maintained in Dulbecco's Modified Eagle's Medium (DMEM) supplemented with 10% fetal calf serum and 1% antibiotics (penicillin/streptomycin). The 50% tissue culture infectious dose ($TCID_{50}$) was determined in MDCK cells after incubation at 37° C. for 3 days and the values were calculated by the method of Reed and Muench (Reed L J, Muench H. A simple method for estimating fifty percent endpoints. American Journal of Hygiene. 1938; 27:493-497). To determine the effectiveness of peptide 5 as shown in SEQ ID NO: 5 in inhibiting virus replication, the pfu/ml was compared with (divided by) the initial pfu/ml that was seeded and expressed as percentage of the initial titer (which was $5\times10^3$ pfu/ml).

B. Viral Titer Determination by Plaque Assay

All viruses used here were initially quantified on MDCK cells to determine infectious titer (plaque forming units per mL, pfu/ml). In brief, the MDCK cells were grown into monolayers in 24-well plates is infected with the virus at $5\times10^3$ pfu/ml after treatment with peptide 5 as shown in SEQ ID NO: 5 (0.001, 0.01, 0.1, 1 and 10 μM). After 1 hr binding at 37° C. on confluent MDCK cells, the unbound virus was gently washed with PBS, and overlaid with 1:1 Noble Agar (1.8%) and 2×DME-F12 (supplemented with Glutamax (Invitrogen, Carlsbad, Calif.), ITS (Invitrogen), and 3 μg/ml acetylated trypsin (Sigma, St. Louis, Mo.)). After allowing agar to solidify, the plates were incubated for ~72 hrs at 37° C. before fixing with crystal violet and counting plaque number at each dilution. After 3 days, the plaque number was counted manually and was normalized against the untreated control (i.e., 0 μM).

Figure 7:
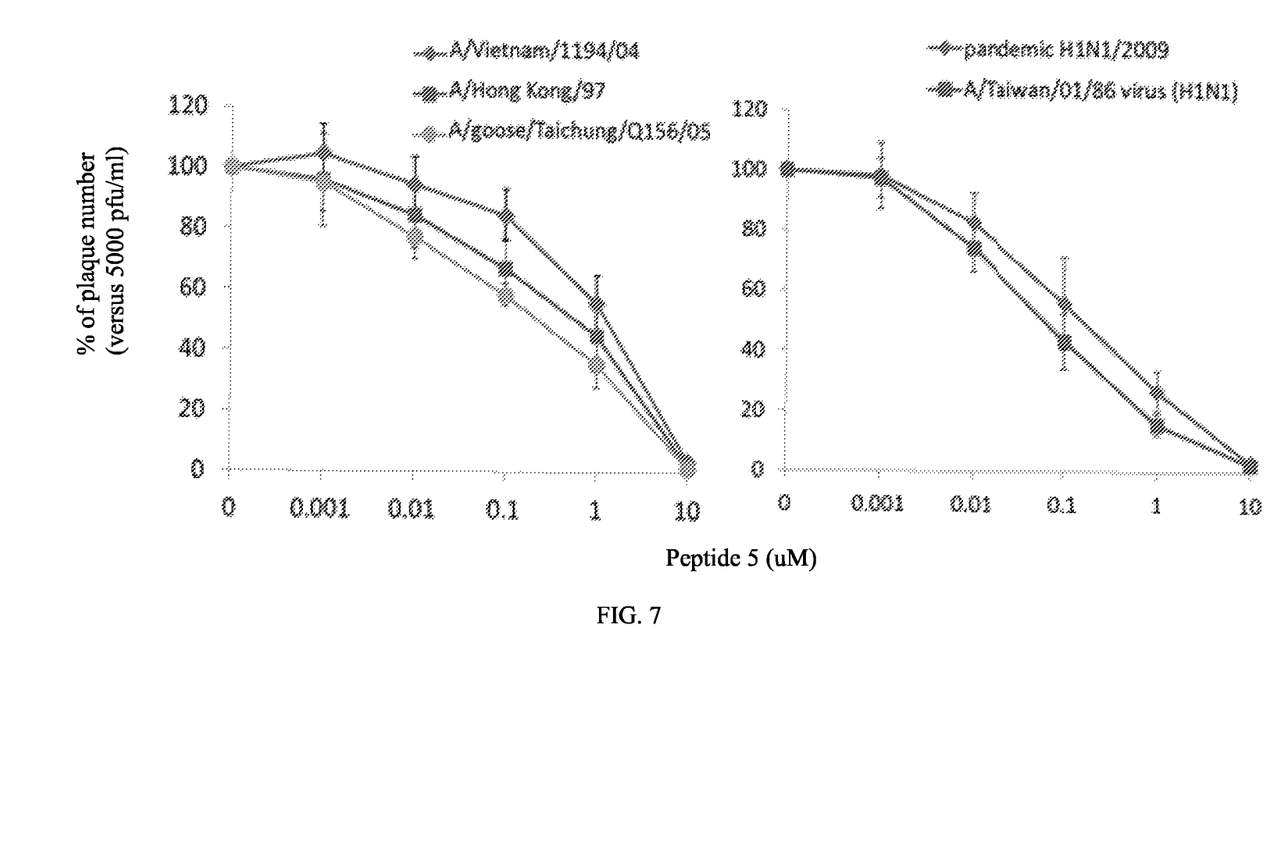

C. Peptide 5 as Shown in SEQ ID NO: 5 Inhibits Influenza Virus H5N1 and H1N1 Replication In Vitro To examine the inhibitory effects of peptide 5 as shown in SEQ ID NO: 5 against the replication of influenza virus H5N1 and H1N1, serially diluted synthetic peptide 5 as shown in SEQ ID NO: 5 was supplemented into the culture of monolayered MDCK cells in 24-well plates which had been exposed to 5000 pfu/ml of H5N1 A/Vietnam/1194/04, A/Hong Kong/97 and A/goose/Taichung/Q156/05, or H1N1. After 3 days, the number of viral plaques with each drug concentration was counted and plaque number was normalized against the untreated control (FIG. 7). It showed that peptide 5 as shown in SEQ ID NO: 5 has potent effects in inhibiting the replication of H5N1 and H1N1 viruses in vitro.

Aspects of the embodiments described herein may be embodied in other forms or carried out in other ways without departing from the spirit or essential characteristics thereof.

The invention claimed is:

1. A method for the inhibition of the activity of an influenza virus in a subject, said method comprising the step of administering to the subject in need thereof an effective amount of a peptide consisting of the amino acid sequence of DEAQETAVSSHEQD (SEQ ID NO: 5).

2. The method of claim 1, wherein the influenza virus is a human influenza virus.

3. The method of claim 1, wherein the influenza virus is an influenza A virus.

4. The method of claim 3, wherein the influenza A virus is selected from the group consisting of H1N1, H1N2, and H5N1.

5. The method of claim 3, wherein the influenza A virus is H1N1.

6. The method of claim 3, wherein the influenza A virus is H5N1.

7. The method of claim 1, wherein the subject is selected from the group consisting of human, non-human mammal, and domestic poultry.

8. The method of claim 1, wherein the subject is human.

9. The method of claim 1, wherein the peptide is a fragment of rabbit α1-antiproteinase F.

10. The method of claim 1, wherein the peptide matches with residues 1-14 of rabbit α1-antiproteinase F.

11. The method of claim 1, wherein the peptide is a recombinant peptide.

12. The method of claim 1, wherein the peptide is a natural peptide.

13. The method of claim 1, wherein the peptide is a synthetic peptide.

* * * * *